United States Patent

Van Tol et al.

(12) United States Patent
(10) Patent No.: US 6,441,210 B1
(45) Date of Patent: Aug. 27, 2002

(54) METAL COMPLEX CONTAINING ONE OR MORE SILSESQUIOXANE LIGANDS

(75) Inventors: Maurits F. H. Van Tol, Limbricht (NL); Sven K. H. Thiele, Halle (DE); Robbert Duchateau, Eindhoven (NL); Hendrikus C. L. Abbenhuis, Nuenen (NL); Rutger A. Van Santen, Eindhoven (NL)

(73) Assignee: DSM N.V., Heerlen (NL)

( * ) Notice: Subject to any disclaimer, the term of this patent is extended or adjusted under 35 U.S.C. 154(b) by 0 days.

(21) Appl. No.: 09/944,158

(22) Filed: Sep. 4, 2001

Related U.S. Application Data

(63) Continuation of application No. 09/740,032, filed on Dec. 20, 2000, which is a continuation of application No. PCT/NL99/00388, filed on Jun. 24, 1999.

(30) Foreign Application Priority Data

Jun. 26, 1998 (EP) ............................................. 98202138

(51) Int. Cl.$^7$ .................................................. C07F 7/08
(52) U.S. Cl. ................... 556/9; 556/10; 528/9
(58) Field of Search ............................ 532/9, 10; 528/9

(56) References Cited

U.S. PATENT DOCUMENTS

| | | | | |
|---|---|---|---|---|
| 4,400,326 A | * | 8/1983 | Daudt et al. ..................... | 556/9 |
| 4,404,196 A | * | 9/1983 | Daudt et al. ..................... | 556/9 |
| 4,510,257 A | * | 4/1985 | Lewis et al. ................. | 556/9 X |
| 4,717,513 A | * | 1/1988 | Lewis et al. ..................... | 556/9 |
| 5,412,053 A | | 5/1995 | Lichtenhan et al. | |

OTHER PUBLICATIONS

Braunstein et al., "Reactions of thiol–functionalized silsesquioxanes with metal carbonyl clusters: syntheses and characterization of . . .", Journal of Organometallic Chemistry, vol. 551, No, 1–2, Jan. 30, 1998, p 125–131.

Duchateau et al., "Half–sandwich titanium complexes stabilized by a novel silsesquioxane ligant: soluble model systems for silica–grafted olefin polymerization catalysts", Organometallics (1998), 17(24), 5222–5224, Nov. 23, 1998.

Duchateau et al., "Ethylene polymerization with dimeric zirconium and hafnium silsesquioxan complexes", Organometallics, 1998, 17(26), pp 5663–5673.

\* cited by examiner

*Primary Examiner*—Paul F. Shaver
(74) *Attorney, Agent, or Firm*—Pillsbury Winthrop LLP

(57) ABSTRACT

Metal complex containing one or more silsesquioxane ligands, having the formula $$Z_y(MA_xB_q)_b \qquad (I),$$

wherein Z is a silsesquioxane according to the formula $$R_{7-l}Si_7O_{12}YD_{1+l} \qquad (II),$$

M is a metal from groups 3–6 of the Periodic System of the Elements and the lanthanides, A is a monoanionic ligand bound to the metal, B is a π-bound ligand, y represents the number of silsesquioxane ligands and is 1–10, b represents the number of metal groups and is 1–20, q is 0,1 or 2, x is the number of substituents A bound to the metal; the value of x depends on the metal used and is equal to the valency of the metal minus 1, 2, 3 or 4, R is a substituent bound to Si, Y is an atom from group 13 or 14 of the Periodic System of the Elements, D is a group, directly bound to Y or Si with one atom from group 15 or 16 of the Periodic System of the Elements and l determines the amount of substituents R and atoms D and is equal to 0, 1, 2 or 3.

7 Claims, No Drawings

METAL COMPLEX CONTAINING ONE OR MORE SILSESQUIOXANE LIGANDS

This is a Continuation of U.S. application Ser. No. 09/740,032 filed Dec. 20, 2000 which is a Continuation of International Application No. PCT/NL99/00388 filed Jun. 24, 1999 which designated the U.S.

The invention is related to a metal complex containing one or more silsesquioxane ligands. Metal complexes containing one or more silsesquioxane ligands are for instance known from FEHER F. J. et al., 'Olefin Polymerization by Vanadium-Containing Polyhedral Oligometallasilsesquioxanes', J. Am. Chem. Soc., 1991, 113, p. 3618–3619.

In this article a vanadium complex is described containing one silsesquioxane ligand. It is reported that this complex is active in the polymerisation of ethylene when it is activated with an aluminum containing co-catalyst.

It is now surprisingly discovered that metal complexes containing a new type of silsesquioxane ligand are also active in olefin polymerisation. The metal complex according to the invention has the formula $$Z_y(MA_xB_q)_b \quad (I),$$

wherein

Z is a silsesquioxane according to the formula $$R_{7-l}Si_7O_{12}YD_{1+l} \quad (II),$$

M is a metal from groups 3–6 of the Periodic System of the Elements and the lanthanides, A is a monoanionic ligand bound to the metal, B is a π-bound ligand, y represents the number of silsesquioxane ligands and is 1–10, b represents the number of metal groups and is 1–20, q is 0,1 or 2, x is the number of substituents A bound to the metal; the value of x depends on the metal used and is equal to the valency of the metal minus 1, 2, 3 or 4, R is a substituent bound to Si, Y is an atom from group 13 or 14 of the Periodic System of the Elements, D is a group, directly bound to Y or Si with one atom from group 15 or 16 of the Periodic System of the Elements and l determines the amount of substituents R and atoms D and is equal to 0, 1, 2 or 3.

A further advantage of the metal complex according to the invention is that polyolefins having a narrow molecular weight distribution can be produced by using these metal complexes.

An other advantage of the metal complex according to the invention is that the metal complexes supported on a carrier material are active in the polymerisation of olefins without the presence of a scavenger.

From Braunstein P et al.: Journal of Organometallic Chemistry, vol. 551, no. 1–2, Jan. 30, 1998 (1998-01-30), page 125–131, metal complexes of the transition metals Ru and Os with thiol-substituted silsesquioxanes are known in which a C-containing spacer between the silsesquioxane and the metal-containing part is always present.

In the following the various components of the metal complex according to the invention will be discussed in more detail.

a) The Silsesquioxane Ligand Z

The silsesquioxane ligand Z is a ligand according to the formula $$R_{7-l}Si_7O_{12}YD_{1+l} \quad (II),$$

wherein

R is a substituent bound to Si,

Y is an atom from group 13 or 14 of the Periodic System of the Elements,

D is a group, directly bound to Y or Si with one atom from group 15 or 16 of the Periodic System of the Elements and l determines the amount of substituents R and atoms D and is equal to 0, 1, 2 or 3.

The silsesquioxane ligand has a cubic structure with all but one Si atom and one atom Y at the corner positions and oxygen atoms connecting the Si and Y atoms. The oxygen atoms are located at the sides of the cubic structure.

A substituent R or an atom D is bound to each Si atom and an atom D is bound to the atom Y. The silsesquioxane ligand can contain 7–4 substituents R and 1–4 groups D.

The silsesquioxane ligand can be represented by the following structure:

In the metal complex according to the invention the silsesquioxane ligand is bound via one atom D to one metal atom. This means that a maximum of 4 metal atoms can be connected via a D atom to the silsesquioxane ligand.

In the metal complex according to the invention 1–10 silsesquioxane ligands can be present (represented by y in formula I).

Y is preferably 1.

R is a substituent bound to Si in the silsesquioxane ligand Z. The R groups can be the same or different and can for instance be hydrogen or an alkyl, aryl or silyl group. R is preferably cyclopentyl, cyclohexyl, cycloheptyl or hydrogen.

Y is an atom from group 13 or 14 of the Periodic System of the Elements and can, for instance, be C, Si, Ge, Sn, B or Al.

D is a group, directly bound to Y or Si with one atom from group 15 or 16 of the Periodic System of the Elements. D can, for instance, be O, S, $NR^1$, $PR^1$, N= or P=, wherein $R^1$ is chosen from hydrogen, alkyl, aryl, silyl or stannyl groups.

Preferably the metal complex according to the invention contains silsesquioxane ligands according to the formula $R_7Si_7O_{12}YD$. These silsesquioxane ligands can only be bound to one metal M with one atom D. In the silsesquioxane ligands Y is preferably Si.

Most preferably the metal complex according to the invention contains a silsesquioxane ligand according to the formula $(RSi)_7O_{12}SiO$. This ligand is bound to the metal M via the oxygen atom.

b) The Metal M

The metals in the complex are chosen from groups 3–6 of the Periodic Table of the Elements and the lanthanides (see the new IUPAC notation to be found on the inside of the cover of the Handbook of Chemistry and Physics, 70th edition, 1989/1990). The metal atoms present in the metal complex according to the invention can be the same or different. In the metal complex according to the invention 1–20 metal atoms can be present (represented by b in formula I). Preferably b is 1.

Preferably M is a metal out of group 4 of the Periodic Table of the Elements.

c) The Mono-anionic Ligand A

The mono-anionic ligand A is bound to the metal. The ligands A can be the same or different and can, for example, be a hydrocarbon ligand containing 1–20 carbon atoms (such as alkyl, aryl, aralkyl, and the like). Examples of such hydrocarbon ligands are methyl, ethyl, propyl, butyl, hexyl, decyl, phenyl, benzyl, and p-tolyl. A ligand A may also be a ligand which in addition to, or instead of, carbon and/or hydrogen contains one or more hetero atoms from groups 14–17 of the Periodic System of the Elements, a hetero atom not being bound directly to the Cp. Thus a ligand may be an N-, O-, and Cl-, or Si-containing group. Examples of ligands containing a hetero atom are trialkylsilyl, triarylsilyl, sulfide, diaryl amido, dialkyl amido, alkoxy or aryloxy groups.

A is preferably an alkyl- or aryl group.

The number of substituents A (represented by x in formula I) depends on the metal used and is equal to the valency of the metal minus 1, 2, 3 or 4. x is preferably 2.

d) The π-bonded Ligand B

The π-bonded ligand is bound to the metal M. The ligands B can be the same or different and can, for example, be an allyl, a cyclopentadienyl, an indenyl, a fluorenyl ligand or a boratabenzene ligand. The above mentioned ligands can be substituted with various substituents. For example with alkyl or aryl substituents containing 1–10 carbon atoms. The ligand B is preferably a substituted or non-substituted cyclopentadienyl ligand. The number of substituents B (represented by q in formula I) and is 0, 1 or 2 per metal atom present in the metal complex. q is preferably 1.

The metal complex according to the invention is preferably a metal complex according to the formula $ZMA_xB$, wherein Z, M, A and B have the meaning as defined above and x is the number of substituents A bound to the metal; the value of x depends on the metal used and is equal to the valency of the metal minus 2.

The metal complex according to the invention can be supported on a carrier material. Examples of suitable carrier materials are any finely divided solid porous support material, including, but not limited to, $MgCl_2$, Zeolites, mineral clays, inorganic oxides such as, for instance, talc, silica, alumina, silica-alumina, meso-porous silica, meso-porous alumosilica, meso-porous alumophospates, inorganic hydroxides, phosphates, sulphates, or resinous support materials such as polyolefins, including polystyrene, or mixtures thereof. These carriers may be used as such or modified, for example by silanes and/or aluminium alkyles and/or aluminoxane compounds.

Preferably the carrier material has a specific surface area of at least 10 m² per gram and a pore volume of at least 0.1 ml per gram. More preferably dehydrated or modified silica such as silylated silica is the carrier material. Most preferably the carrier material is silica or meso-porous silica. The silica carrier material can also be modified before with the co-catalyst; for instance methylaluminoxane.

The invention is also directed to a new type of silsesquioxane compounds of the formula $$R_{7-l}Si_7O_{12}Y(DR')_{1+l} \qquad (III),$$

wherein the symbols have the meaning as defined above and R' is a substituent bound to D and can be chosen from hydrogen, a trialkylsilyl group or a trialkylstannyl group.

Preferably the silsesquioxane compounds are compounds according to the formula $R_7Si_7O_{12}YDR'$

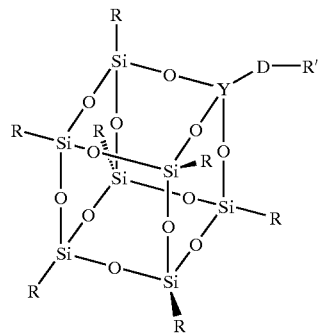

The new silsesquioxane compounds can be prepared according to the following method of synthesis. a silsesquioxane compound according to the formula $$R_{7-l}Si_7O_{12}H_3(OH)_l \qquad (IV),$$

is reacted with a compound $YR''_4$ and that the reaction product that is obtained, $R_{7-l}Si_7O_{12}YR''(OH)_l$, is thereafter reacted with a compound $DR'_2$, wherein D and Y have the meaning as defined above, R" is a group bound to Y.

Preferably a silsesquioxane compound according to the formula $$R_7Si_7O_{12}H_3 \qquad (V),$$

is reacted with a compound $YR''_4$ and that the reaction product that is obtained, $R_7Si_7O_{12}YR''$, is thereafter reacted with a compound $DR'_2$, wherein D and Y have the meaning as defined above, R" is a group bound to Y. The compounds according to formula IV and V can be prepared by addition of excess water to a vigorously stirred solution of the appropriate trichlorosilane, $RSiCl_3$, in an organic solvent. This method is, for instance, described in FEHER R. J. et al., J. Am. Chem. Soc., 111 (1989), p.1741–1748. The compounds according to formula IV are preferably purified before using in further reactions. Purification methods known to the man skilled in the art can be used. The compound $YR''4$ contains 4 R" groups. The R" groups are the same or different and are halide atoms, for example Cl or Br. The reaction can be carried out in a solvent, for example, tetrahydrofurean, ethers or toluene. The silsesquioxane compound according to formula III is isolated after the reaction, for example by filtering off the solid from the reaction mixture or by crystallisation.

The metal complex according to the invention can be prepared by reacting 1 to 5 equivalents of a ligand with the formula $$R_{7-l}Si_7O_{12}Y(DR')_{1+l} \qquad (III),$$

with 1–5 equivalents $MA_xB_qX_c$ wherein the symbols have the meaning as defined in claim 1, R' is a substituent bound to D, X is a monoanionic substituent that is able to react with R' and c is 1 or 2.

The monoanionic substituent X can be the same or different and can, for example, be a hydrocarbon radical containing 1–20 carbon atoms (such as alkyl, aryl, aralkyl, and the like). Examples of such hydrocarbon radicals are methyl, ethyl, propyl, butyl, hexyl, decyl, phenyl, benzyl, and p-tolyl. X can also be a dialkyl amido substituent. The substituents A on the metal can be the same as the substituents X. The reaction can be carried out in a solvent, for example, pentane, hexane, toluene, diethyl ether and tetrahydrofurane. The reaction is normally performed under an inert gas (nitrogen or argon) at room temperature and at atmospheric pressure. The concentration of the reactants is not of primary importance, but convenient concentrations are in the region of 0.01–0.1 M for each reactant when X is cyclohexyl, and 0.001–0.005 M for each reactant when X is cyclopentyl or cycloheptyl especially. Isolation of the metallasilsesquioxane product is most conveniently accomplished by removing the volatile material present (i.e. solvent and reaction sideproduct) under reduced pressure. Analytically pure material is obtained by crystallization from concentrated cooled hydrocarbon solvents. If the complex is to be transferred directly into a catalyst, then it is most conveniently generated in situ and used without further purification.

Supported catalyst systems of the invention may be prepared by several methods. The metal complex and eventually the co-catalyst can be mixed together before the addition of the support material. The mixture may be prepared in conventional solution in a normally liquid alkane or aromatic solvent. The solvent is preferably also suitable for use as a polymerization diluent for the liquid phase polymerization of an olefin monomer. Alternatively, the co-catalyst can be placed on the support material followed by the addition of the metal complex or conversely, the metal complex may be applied to the support material followed by the addition of the co-catalyst. The co-catalyst can be used as commercially supplied, or may be generated in situ on the solid support. The supported catalyst may be prepolymerized. In addition third components can be added in any stage of the preparation of the supported catalyst. Third components can be defined as compounds containing Lewis acidic or basic functionalities exemplified but not limited to compounds such as N.N-dimethylaniline, tetraethoxysilane, phenyltriethoxysilane, bis-tert-butylhydroxy toluene (BHT) and the like.

The solid-phase immobilization (SPI) technique described by H. C. L. Abbenhuis in *Angew. Chem. Int. Ed.* 37 (1998) 356–58, by M.Buisio et al. in *Microporous Mater.*, 5 (1995) 211 and by J. S. Beck et al. in *J. Am. Chem. Soc.*, 114 (1992) 10834 as well as the pore volume impregnation (PVI) technique (see WO 97/24344) can be used to support the metal complex on to the carrier material. The isolation of the impregnated carrier can be done by filtration or by removing the volatile material present (i.e. solvent) under reduced pressure.

The metal complex according to the invention can be used, without activation with a co-catalyst, for the polymerisation of olefins. The metal complex can also be activated using a co-catalyst. The activation can be performed during a separate reaction step including an isolation of the activated compound or can be performed in situ. The activation is preferably performed in situ because after the activation of the metal complex separation and/or purification of the activated complex is not necessary.

The metal complexes according to the invention can be activated using suitable co-catalysts. For example, the co-catalyst can be an organometallic compound, wherein at least one hydrocarbon radical is bound directly to the metal to provide a carbon-metal bond. The hydrocarbon group used in the organometallic compounds preferably contains 1–30, more preferably 1–10 carbon atoms. The metal of the organometallic compound can be selected from group 1, 2, 3, 12, 13 or 14 of the Periodic Table of the Elements. Suitable metals are, for example, sodium, lithium, zinc, magnesium and aluminium and boron.

Examples of suitable co-catalysts are alkyl sodium, alkyl lithium, alkyl zinc, alkyl magnesium halide, dialkyl magnesium, organoaluminum compounds and halogen-containing organoaluminum compounds. Examples of organoaluminum compounds are triaryl and trialkyl aluminum compounds, such as triethyl aluminum and tri-isobutyl aluminum; alkyl aluminum hydrides, such as di-isobutyl aluminum hydride; alkylalkoxy organoaluminum compounds; and halogen-containing organoaluminum compounds, such as diethyl aluminum chloride, diisobutyl aluminum chloride and ethyl aluminum sesquichloride. Linear or cyclic aluminoxanes can also be used as co-catalyst.

The metal complex according to the invention can also be activated with a compound which contains or yields in a reaction with the metal complex of the present invention a non-coordinating or poorly coordinating anion. Such compounds have been described for instance in EP-A-426,637, the complete disclosure of which is incorporated herein by reference. Such an anion is bound sufficiently unstable such that it is replaced by an unsaturated monomer during the polymerization. Such compounds are also mentioned in EP-A-277,003 and EP-A-277,004, the complete disclosures of which are incorporated herein by reference. Such a compound preferably contains a triaryl borane or a tetraaryl borate or an aluminum equivalent thereof. Examples of suitable co-catalyst compounds include, without limitation, the following:

dimethyl anilinium tetrakis(pentafluorophenyl)borate $[C_6H_5N(CH_3)_2H]^+[B(C_6F_5)_4]^-$;
dimethyl anilinium bis(7,8-dicarbundecaborate)cobaltate (III);
tri(n-butyl)ammonium tetraphenyl borate;
triphenylcarbenium tetrakis(pentafluorophenyl)borate;
dimethylamilinium tetraphenyl borate;
tetrakis(pentafluorophenyl)borate;
tris(pentafluorophenyl)borane and
tris[3,5-bis(trifluormethyl)]borane.

If the above-mentioned non-coordinating or poorly coordinating anion is used as the co-catalyst, it is preferable for the metal compound according to the invention to be alkylated (that is, one of the A groups is an alkyl-or aryl group). Co-catalysts containing boron are preferred. Most preferred are co-catalysts containing tetrakis(pentafluorophenyl) borate, tris(pentafluorophenyl)borane or tetrakis(3,5-bistrifluoromethyl-phenyl)borate.

When a boron containing co-catalyst is used the polymerisation time is longer than when an other co-catalyst is used for the homogeneous polymerisation of olefins. The molar ratio of the co-catalyst relative to the metal center in the metal complex in case an organometallic compound is selected as the co-catalyst, usually is in a range of from about 1:10 to about 10,000:1, and preferably is in a range of from about 1:1 to about 2,500:1. If a compound containing or yielding a non-coordinating or poorly coordinating anion is selected as co-catalyst, the molar ratio usually is in a range of from about 1:100 to about 1,000:1, and preferably is in range of from about 1:2 to about 250:1.

In addition to the metal complex according to the invention and the co-catalyst the catalyst composition can also contain a small amount of an other organometallic compound that is used as a so called scavenger. The scavenger is added to react with impurities in the reaction mixture. It is normally added to the reaction mixture before addition of the metal complex and the co-catalyst. Usually organoaluminum compounds are used as a scavenger. Examples of scavengers are trioctylaluminium, triethylaluminium and tri-isobutylaluminium. As a person skilled in the art would be aware, the metal complex as well as the co-catalyst can be present in the catalyst composition as a single component or as a mixture of several components. For instance, a mixture may be desired where there is a need to influence the molecular properties of the polymer, such as molecular weight distribution.

The metal complex according to the invention can be used for the polymerization of olefin monomers. The olefin envisaged in particular is an olefin chosen from the group comprising a-olefin, internal olefin, cyclic olefin and di-olefin. Mixtures of these can also be used.

The metal complex according to the invention is in particular suitable for a process for the polymerization of an α-olefin. In particular the α-olefin monomer(s) is/are chosen from the group comprising ethene, propene, butene, pentene, heptene, hexene and octene (substituted or non-substituted), mixtures of which may also be used. More preferably, ethene and/or propene is used as α-olefin. The use of such olefins results in the formation of (semi)crystalline polyethene homo- and copolymers, of high as well as of low density (HDPE, LDPE, LLDPE, etc.), and polypropene, homo- and copolymers (PP and EMPP). The monomers needed for such products and the processes to be used are known to the person skilled in the art.

With the metal complex according to the invention amorphous or rubber-like copolymers based on ethene and another α-olefin can also be prepared. Propene is preferably used as the other α-olefin, so that EPM rubber is formed. It is also quite possible to use a diene besides ethene and the other α-olefin, so that a so-called EADM rubber is formed, in particular EPDM (ethene propene diene rubber).

Polymerization of the a-olefin monomer(s) can be effected in a known manner, in the gas phase as well as in a liquid reaction medium. In the latter case, both solution and suspension polymerization are suitable. The supported catalyst systems according to the invention are used mainly in gas phase and slurry processes. The quantity of metal to be used generally is such that its concentration in the dispersion agent amounts to $10^{-8}$–$10^{-3}$ mol/l, preferably $10^{-7}$–$10^{-4}$ mol/l.

The invention will hereafter be elucidated with reference to polymerisations of α-olefins known per se, which are representative of the polymerization referred to in the present description. For the preparation of other polymers on the basis of α-olefin monomers the reader is expressly referred to the multitude of publications on this subject.

The polymerisation process can be conducted as a gas phase polymerisation (e.g. in a fluidized bed reactor), as suspension/slurry polymerisation, as a solid phase powder polymerisation or as a so called bulk polymerisation process, in excess of olefinic monomer used as the reaction medium. Dispersion agents may suitably be used for the polymerisation, which may in particular, but not limited to, be chosen from saturated, straight or branched aliphatic hydrocarbons, such as butanes, pentanes, hexanes, heptanes, pentamethyl heptane or mineral oil fractions such as light or regular petrol, naphtha, kerosine or gas oil. Also fluorinated hydrocarbons or similar liquids are suitable for that purpose. Aromatic hydrocarbons, for instance benzene and toluene, can be used, but because of their cost as well as on account of safety considerations, it will be preferred not to use such solvents for production on a technical scale. In polymerization processes on a technical scale, it is preferred therefore to use as solvent the low-priced aliphatic hydrocarbons or mixtures thereof, as marketed by the petrochemical industry.

If an aliphatic hydrocarbon is used as solvent, the solvent may yet contain minor quantities of aromatic hydrocarbon, for instance toluene. Thus, if for instance methyl aluminoxane (MAO) is used as co-catalyst, toluene can be used as solvent for the MAO in order to supply the MAO in dissolved form to the polymerization reactor. Drying or purification of the solvents is desirable if such solvents are used; this can be done without problems by the average person skilled in the art.

In the polymerisation process the metal complex and the co-catalyst are used in a catalytically effective amount, i.e. any amount that succesfully results in the formation of polymer. Such amounts may be readily determined by routine experimentation by the skilled art worker.

Those skilled in the art will easily understand that the catalyst systems used in accordance with this invention may also be prepared in-situ.

If a solution or bulk polymerisation is to be used it is preferably carried out at temperatures well above the melting point of the polymer to be produced, typically, but not limited to, temperatures between 120° C. and 260° C.

The polymeirsation process can also be carried out under suspension or gasphase polymerization conditions which typically take place at temperatures well below the melting temperature of the polymer to be produced, typically, but not limited to, temperatures below 105° C.

The polymer resulting from the polymerization can be worked up by a method known per se. In general the catalyst is de-activated at some point during the processing of the polymer. The de-activation is also effected in a manner known per se, e.g. by means of water or an alcohol. Removal of the catalyst residues can mostly be omitted because the quantity of catalyst in the polymer, in particular the content of halogen and metal is very low now owing to the use of the catalyst system according to the invention.

Polymerization can be effected at atmospheric pressure, at sub-atmospheric pressure, or at elevated pressure of up to 500 MPa, continuously or discontinuously. Preferably, the polymerization is performed at pressures between 0.01 and 500 MPa, most preferably between 0.01 and 10 MPa, in particular between 0.5–3 MPa. Higher pressures can be applied. In such a high-pressure process the metal complex according to the present invention can also be used with good results. Slurry and solution polymerisation normally take place at lower pressures, preferably below 20 MPa.

The polymerization can also be performed in several steps, in series as well as in parallel. If required, the catalyst composition, temperature, hydrogen concentration, pressure, residence time, etc. may be varied from step to step. In this way it is also possible to obtain products with a wide molecular weight distribution. By using the metal complexes according to the present invention for the polymerisation of olefins polymers are obtained with a polydispersity (Mw/Mn) of 1.5–50. It is an advantage that also polymers with a narrow polydispersity can be produced, i.e polymers with a polydispersity of 1.5–2.5.

The invention also relates to a polyolefin polymer which can be obtained by means of the polymerization process according to the invention.

The invention will now be illustrated by means of the following non-restrictive examples.

EXAMPLES

General

All tests in which organometallic compounds were involved were carried out in an inert nitrogen atmosphere, using standard Schlenk equipment. In the following THF stands for tetrahydrofurane, TMEDA means tetramethylethylenediamine, 'Me' means 'methyl', 'Et' means 'ethyl', 'Bu' means 'butyl', 'Cp' means 'cyclopentadienyl', 'Cp"' means 'bis-1,3-trimethylsilylcyclopentadienyl' Pressures mentioned are absolute pressures. The products were characterized by means of SEC-DV (size exclusion chromatography), Elemental Analysis and NMR with a Bruker ACP 200 ($^1$H=400 MHz; $^{13}$C=100 MHz) Mn and Mw are molecular weights determined by universal calibration of SEC-DV.

Example I

Preparation of $(c-C_5H_9)_7Si_8O_{12}(OH)$ (1)

A suspension of $(c-C_5H_9)_7Si_8O_{12}Cl$ (2.11 g, 2.25 mmol) in THF/H$_2$O (3:2, 50 mL) was refluxed for 40 hour. Evaporation of the volatiles afforded crude 1 as a white solid. Stripping with toluene (2×5 mL) was required to remove the present lattice THF. Thorough drying and recrystallization from a hot toluene/acetonitrile mixture gave analytically pure 1 as a white microcrystalline material (1.65 g, 1.80 mmol, 80%). IR (Nujol, cm$^{-1}$): 3650 (br, OH). Anal. Calcd. for $C_{35}H_{64}O_{13}Si_8$: C, 45.81; H, 7.03. Found: C, 44.87; H, 7.09.

Example II

Preparation of $[(c-C_5H_9)_7Si_8O_{13}]Li$ (2)

At room temperature, n-BuLi (0.9 mL 2.5 M in hexanes, 2.25 mmol) was added to a solution of 1 (2.08 g, 2.27 mmol) in hexanes (50 mL). After stirring for 0.5 hour the solvent was evaporated leaving 2 as a white foam (1.87 g, 2.0 mmol, 89%). Due to the extreme solubility of 2 in common organic solvents purification by means of recrystallization proved to be impossible.

Example III

Preparation of $[(c-C_5H_9)_7Si_8O_{13}]Li.TMEDA$ (3)

At room temperature a solution of 2 (4.38 g, 4.77 mmol) in ether (30 mL) was treated with TMEDA (1.5 mL, 10 mmol) and BuLi (1.9 mL, 4.75 mmol, 2.5 M in hexanes). After a few minutes, needle shaped crystals of 3 started to form. Subsequent cooling to +40° C. yielded 1.72 g (1.65 mmol, 35%) of 3. $^1$H NMR (CDCl$_3$, δ): 2.38 (s, 4H, CH$_2$-TMEDA), 2.32 (s, 12H, CH$_3$-TMEDA), 1.75 (m, 14H, CH$_2$—C$_5$H$_9$), 1.52 (m, 42H, CH$_2$—C$_5$H$_9$), 0.96 (m, 7H, CH—C$_5$H$_9$). $^{13}$C NMR (CDCl$_3$, δ): 56.86 (t, CH$_2$-TMEDA, $^1J_{C-H}$=133 Hz), 45.86 (q, CH$_3$-TMEDA, $^1J_{C-H}$=137 Hz). $^{13}$C{$^1$H} NMR (CDCl$_3$, δ): 27.74, 27.34, 27.28, 27.18, 27.07 (s, CH$_2$—C$_5$H$_9$), 22.71, 22.41 (s, CH—C$_5$H$_9$). $^{29}$Si{$^1$H} NMR (toluene, δ):.−66.75, −68.35, −103.67 (4:3:1). Anal. Calcd. (found) for $C_{41}H_{79}LiN_2O_{13}Si_8$: C, 47.36; (47.00); H, 7.66; (7.74); N, 2.69; (2.27).

Example IV

Preparation of $[(c-C_5H_9)_7Si_8O_{13}]Tl$ (4)

To a solution of 1 (3.5 g, 3.8 mmol) in toluene (25 mL) TlOEt (0.27 mL, 3.8 mmol) was added at room temperature. The mixture was left overnight after which the volatiles were removed in vacuo leaving crude 4 as a white foam. Recrystallization at −30° C. from hexane yielded 4 as thin colorless needles (2.2 g, 1.96 mmol, 52%). $^1$H NMR (CDCl$_3$, δ): 1.78 (m, 14H, CH$_2$—C$_5$H$_9$), 1.54 (m, 42H, CH$_2$—C$_5$H$_9$), 1.00 (m, 7H, CH—C$_5$H$_9$). $^{13}$C{$^1$H} NMR (CDCl$_3$, δ): 27.36, 27.32, 27.21, 27.07 (s, CH$_2$—C$_5$H$_9$), 22.33, 22.30, 22.27 (s, CH—C$_5$H$_9$, 3:1:3). $^{29}$Si{$^1$H} NMR (CH$_2$Cl$_2$, δ): −67.06, −67.31, −101.23 (s, 4:3:1). Anal. Calcd. (found) for $C_{35}H_{63}O_{13}Si_8Tl$: C, 37.50; (37.64); H, 5.67; (5.65).

Example V

Preparation of $Cp"[(c-C_5H_9)_7Si_8O_{13}]TiCl_2$ (5)

BuLi (3.4 mL, 2.5 M in hexanes, 8.5 mmol) was added to a hexane solution of 1 (7.7 g, 8.4 mmol). Subsequently, cp"TiCl$_3$ (3.07 g, 8.44 mmol) was added to the in situ prepared solution of $[(c-C_5H_9)_7Si_8O_{13}]Li$ and the mixture was stirred overnight at room temperature. Filtration, concentration and cooling to −30° C. yielded a yellow powder consistent of a 9:1 mixture of 5 and 6. Repeated recrystallisation from hexane yielded analytically pure 5 (5.3 g, 4.3 mmol, 51%). Anal. Calcd. for $C_{46}H_{84}Cl_2O_{13}Si_{10}Ti$: C, 44.38; H, 6.80; Ti, 3.85. Found: C, 44.20; H, 6.87; Ti, 3.85.

Example VI

Preparation of $Cp"[(c-C_5H_9)_7Si_8O_{13}]_2TiCl$ (6)

A solution of 2 (4.2 g, 4.6 mmol) in hexane (50 mL) was treated with Cp"TiCl$_3$ (0.79 g, 2.17 mmol) and the resulting suspension was stirred for two days at room temperature. The salt was removed by centrifuge and the solvent was evaporated yielding 6 (3.6 g, 1.7 mmol, 78%) as a bright yellow foam. Anal. Calcd. for $C_{81}H_{147}ClO_{26}Si_{18}Ti$: C, 45.76; H, 6.97; Ti, 2.25. found: C, 45.36; H, 7.07; Ti, 2.19.

Example VII

Preparation of $Cp"[(c-C_5H_9)_7Si_8O_{13}]Ti(CH_2Ph)_2$ (7)

To a hexane (25 mL) solution of Cp"Ti(CH$_2$Ph)$_3$ (1.21 g, 2.28 mmol) was added solid 1 (2.10 g, 2.26 mmol) at 0° C. and the mixture was warmed to room temperature. After stirring for 2 hours, traces of insoluble impurities were filtered off and the dark red solution was concentrated to approx. 5 mL. Crystallization at −30° C. afforded 7 as red microcrystalline material (2.0 g, 1.5 mmol, 66%). Anal. Calcd. for $C_{60}H_{98}O_{13}Si_{10}Ti$: C, 53.14; H, 7.28; Ti, 3.53. Found: C, S2.81; H, 7.19; Ti, 3.47.

Example VIII

Preparation of $Cp"[(c-C_5H_9)_7Si_8O_{13}]TiMe_2$ (8)

Cp"TiMe$_3$ (1.04 g, 3.44 mmol) was dissolved in hexane (25 mL) and cooled to −90° C. Silanol 1 (3.09 g, 3.3 mmol) was added and the mixture was allowed to slowly warm to room temperature. Evaporation of the solvent afforded 8 as a yellow foam. Slow crystallization from hexane at −30° C. yielded 8 (2.1 g, 1.7 mmol, 51%) as yellow crystalline material. $^1$H NMR (C$_6$D$_6$, δ): 7.17 (s, 1H, C$_5$H$_3$(SiMe$_3$)$_2$), 6.63 (s, 2H, C$_5$H$_3$(SiMe$_3$)$_2$), 1.68 (m, 56 H, CH$_2$—C$_5$H$_9$), 1.30 (m, 7H, CH—C$_5$H$_9$), 1.01 (s, 6H, CH$_3$), 0.24 (18H, Si(CH$_3$)$_3$). $^{13}$C NMR (C$_6$D$_6$, δ): 131.16 (s, C$_5$H$_3$(SiMe$_3$)$_2$), 124.71 (d, C$_5$H$_3$(SiMe$_3$)$_2$, $^1J_{C-H}$=163 Hz), 123.22 (d, C$_5$H$_3$(SiMe$_3$)$_2$, $^1J_{C-H}$=164 Hz), 56.56 (q, CH$_3$, $^1J_{C-H}$=123 Hz), 27.94, 27.85, 27.50 (t, CH$_2$—C$_5$H$_9$, $^1J_{C-H}$=130 Hz), 22.88, 22. 77 (d, CH—C$_5$H$_9$, $^1J_{C-H}$=122 Hz), −0.23 (q, Si(CH$_3$)$_3$, $^1J_{C-H}$=120 Hz). $^{29}$Si NMR (toluene, δ): −8.35, −66.26, −66.65, −111.06 (2:3:4:1). Anal. calcd. (found) for $C_{48}H_{90}O_{13}Si_{10}Ti$: C, 47.88 (47.63); H, 7.53 (7.49); Ti, 3.98 (3.67).

Example IX

Preparation of $Cp"[(c-C_5H_9)_7Si_8O_{13}]ZrCl_2$ (9)

Toluene (30 mL) was added to a mixture of 4 (1.90 g, 1.70. mmol) and Cp"ZrCl$_3$ (0.70 g, 1.70 mmol). The formed white suspension was stirred overnight. After the volatiles were removed in vacuo, the crude product was stripped (10 mL) and extracted (30 mL) with hexane. Evaporation of the solvent yielded a white foam. $^1$H NMR spectroscopy revealed that a 2:1 mixture of Cp"[(c-C$_5$H$_9$)$_7$Si$_8$O$_{13}$]ZrCl$_2$ (9) and Cp"[(c-C$_5$H$_9$)$_7$Si$_8$O$_{13}$]$_2$ZrCl (10) was formed. Due to their extreme solubility, separation of these products proved to be difficult. Cp"((c-C$_5$H$_9$)$_7$Si$_8$O$_{13}$]ZrCl$_2$: $^1$H NMR (CDCl$_3$, δ): 7.14 (t, 1H, C$_5$H$_3$(SiMe$_3$)$_2$, $^4J_{H-H}$=2 Hz), 7.03 (d, 2H, C$_5$H$_3$(SiMe$_3$)$_2$, $^4J_{H-H}$=2 Hz), 1.80 (m, 14H, CH$_2$—C$_5$H$_9$), 1.56 (m, 42H, CH$_2$—C$_5$H$_9$), 1.18 (m, 7H, CH—C$_5$H$_9$), 0.39 (s, 18H, C$_5$H$_3$(Si(CH$_3$)$_3$)$_2$). $^{13}$C{$^1$H} NMR (CDCl$_3$, δ): 135.24 (s, C$_5$H$_3$(SiMe$_3$)$_2$), 130.09 (s, C$_5$H$_3$(SiMe$_3$)$_2$), 126.17 (s, C$_5$H$_3$(SiMe$_3$)$_2$), 27.32 (s, CH$_2$—C$_5$H$_9$), 27.26 (s, CH$_2$—C$_5$H$_9$) 27.01 (s, CH$_2$—C$_5$H$_9$), 22.13 (s, CH—C$_5$H$_9$), −0.49 (s, C$_5$H$_3$(Si(CH$_3$)$_3$)$_2$). $^{29}$Si{$^1$H} NMR (THF, δ): −7.36, −66.68, −66.84, −111.40 (2:3:4:1).

Example X

Preparation of Cp"[(c-C$_5$H$_9$)$_7$Si$_8$O$_{13}$]$_2$ZrCl (10)

At room temperature, a toluene (40 mL) solution of Cp"ZrCl$_3$ (0.77 g, 1.89 mmol) was treated with 2 equiv. of 4 (4.24 g, 3.78 mmol). Immediately, a white precipitate was formed. The mixture was stirred overnight. The volatiles were evaporated and the product stripped with hexane (10 mL). The product was redissolved in hexane (50 mL) and after centrifuging to remove the TlCl, the solvent was removed in vacuo leaving 10 as an off-white foam (2.90 g, 1.34 mmol, 71%). $^1$H NMR (CDCl$_3$, δ): 7.13 (t, C$_5$H$_3$(SiMe$_3$)$_2$, $^4J_{H-H}$=2 Hz), 6.95 (d, C$_5$H$_3$(SiMe$_3$)$_2$, $^4J_{H-H}$=2 Hz), ), 1.80 (m, 14H, CH$_2$—C$_5$H$_9$), 1.56 (m, 42H, CH$_2$—C$_5$H$_9$), 0.95 (m, 7H, CH—C$_5$H$_9$), 0.36 (s, 18H, C$_5$$_{H3}$(Si(CH$_3$)$_3$)$_2$). $^{13}$C{$^1$H} NMR (CDCl$_3$, δ): 132.15 (s, C$_5$H$_3$(SiMe$_3$)$_2$), 124.80 (s, C$_5$H$_3$(SiMe$_3$)$_2$), 27.32, 27.27, 27.04 (s, CH$_2$—C$_5$H$_9$), 22.25, 22.19, 22.12 (s, 1:3:3, CH—C$_5$H$_9$), −0.44 (s, C$_5$H$_3$(Si(CH$_3$)$_3$)$_2$). $^{29}$Si NMR (toluene, δ): −7.85, −65.88, −66.42, −109.74 (1:3:4:1). Anal. Calcd. (found) for C$_{81}$H$_{147}$ClO$_{26}$Si$_{18}$Zr: C, 44.85 (44.47); H, 6.83 (6.93); Zr, 4.21 (4.09).

Example XI

Preparation of [(c-C$_5$H$_9$)$_7$Si$_8$O$_{13}$]TiCl$_3$ (11)

At room temperature, a solution of 1 (2.92 g, 3.18 mmol) in hexane (30 mL) was added to a hexane (50 mL) solution of TiCl$_4$ (1.5 mL, 13.7 mmol). Upon addition the reaction mixture turned reddish and colorless microcrystalline material precipitated. The volatiles were removed in vacuo and the crude product was dissolved in hot toluene (20 mL). Crystallization at room temperature yielded 11 as block shaped off white crystals (1.2 g, 1.1 mmol, 35%). Cooling of the mother liquor to −30° C. yielded a second crop of 11 as white microcrystalline material (1.65 g, 1.5 mmol, 48%). $^1$H NMR (CDCl$_3$, δ): 1.80 (m, 14H, CH$_2$—C$_5$H$_9$), 1.55 (m, 42H, CH$_2$—C$_5$H$_9$), 1.07 (m, 7H, CH—C$_5$H$_9$). $^{13}$C NMR (CDCl$_3$, δ): 27.21 (t, CH$_2$—C$_5$H$_9$, $^1J_{C-H}$=129 Hz), 27.16 (t, CH$_2$—C$_5$H$_9$, $^1J_{C-H}$=129 Hz), 26.95 (t, CH$_2$—C$_5$H$_9$, $^1J_{C-H}$=129 Hz), 22.09 (d, CH—C$_5$H$_9$, $^1J_{C-H}$=119 Hz), 22.00 (d, CH—C$_5$H$_9$, $^1J_{C-H}$=119 Hz), 21.80 (d, CH—C$_5$H$_9$, $^1J_{C-H}$=121 Hz). $^{29}$Si NMR (CH$_2$Cl$_2$, δ): −65.82, −67.04, −113.48. Anal. calcd. (found) for C$_{35}$H$_{63}$Cl$_3$O$_{13}$Si$_8$Ti: C, 39.26 (39.72); H, 5.93 (6.04); Ti, 4.47 (4.25).

Example XII

Preparation of [(c-C$_5$H$_9$)$_7$Si$_8$O$_{13}$]TiCl$_3$.THF(12)

At room temperature, a hexane solution of 1 (1.9 g, 2.1 mmol) was added to a solution of TiCl$_4$ (1 mL, 9.1 mmol) in hexane 930 mL). After removal of the volatiles, the remaining solid was dissolved in a 3:1 mixture of hexane/THF (40 mL). Cooling to −30 yielded 12 (1.3 g, 1.1 mmol, 52%) as a white microcrystalline material. $^1$H NMR (C$_6$D$_6$, δ): 4.08 (m, 8H, α-CH$_2$-THF), 1.89 (m, 21H, CH$_2$—C$_5$H$_9$), 1.71 (m, 21H, CH$_2$—C$_5$H$_9$), 1.50 (m, 14H, CH$_2$—C$_5$H$_9$), 1.32 (8H, β-CH$_2$-THP), 1.18 (m, 7H, CH— C$_5$H$_9$). $^{13}$C{$^1$H} NMR (C$_6$D$_6$): 74.1 (s, α-CH$_2$-THF), 27.75, 27.72, 27.38 (s, CH$_2$—C$_5$H$_9$), 25.26 (s, β-CH$_2$-THF), 22.64, 22.57 (s, CH—C$_5$H$_9$). $^{29}$Si NMR (CH$_2$Cl$_2$, δ): −66.50, −66.99, −112.34.

Example XIII

Preparation of the Polymerization Catalyst 13

2 ml of a toluene solution containing 1*10$^{-5}$ mol of complex 7 was contacted with 2 ml of a toluene solution containing 1*10$^{-5}$ mol triphenylcarbenium-tetrakis-(pentafluorophenyl)borate Ph$_3$C[B(C$_6$F$_5$)$_4$]. After stirring the solution for 10 minutes the polymerization catalyst 13 was formed. The polymerization catalyst 13 can be stored for weeks, if the toluene solvent was removed.

Example XIV

Preparation of the Polymerization Catalyst 14

2 ml of a toluene solution containing 2*10$^{-5}$ mol of complex 7 was contacted with 1 ml of a toluene solution containing 2*10$^{-5}$ mol tris-(pentafluorophenyl)borane [B(C$_6$F$_5$)$_3$]. After stirring the solution for 10 minutes the polymerization catalyst 14 was formed. The polymerization catalyst 14 can be stored for weeks at low temperatures, if the toluene solvent was removed.

Example XV

Preparation of the Polymerization Catalyst 15

2 ml of a toluene solution containing 2*10$^{-5}$ mol of complex 8 was contacted with 1 ml of a toluene solution containing 2*10$^{-5}$ mol tris-(pentafluorophenyl)borane [B(C$_6$F$_5$)$_3$]. After stirring the solution for 10 minutes the polymerization catalyst 15 was formed. The polymerization catalyst 15 can be stored for weeks at low temperatures, if the toluene solvent was removed.

Example XVI

Preparation of the Supported Polymerization Catalyst 16 (Wet Method)

1 ml of a toluene solution containing 1.5*10$^{-5}$ mol of complex 8 was adsorbed on 0.5 g silica PQ3030 containing MAO (aluminum content of the silica: 0.123 g, (4.6*10$^{-3}$ mol)), stirred for 3 hour.

Example XVII

Preparation of the Supported Polymerization Catalyst 17 (Dry Method)

1 ml of a toluene solution containing 1.5*10$^{-5}$ mol of complex 8 was adsorbed on 0.5 g silica PQ3030 containing MAO (aluminum content of the silica: 0.123 g, (4.6*10$^{-3}$ mol)), stirred for 3 hour and dried in the vacuum. The polymerization catalyst 17 can be stored for weeks at low temperatures.

Example XVIII

Preparation of the Supported Polymerization Catalyst 18 (Dry Method)

1 ml of a toluene solution containing 1.5*10$^{-5}$ mol of complex 7 was adsorbed on 0.5 g silica PQ3030 containing MAO (aluminum content of the silica: 0.123 g, (4.6*10$^{-3}$ mol)), stirred for 3 hour and dried in the vacuum. The polymerization catalyst 18 can be stored for weeks at low temperatures.

Polymerization Reactions

Example IXX

Ethylene Polymerization Using the Polymerization Catalyst 14

General Procedure 600 ml of an alkane mixture were brought as solvent under dry nitrogen in a stainless steel reactor having a volume of 1.5 liter. The reactor was than heated under constant mixing to the required temperature of 80° C. under an absolute pressure of ethylene of 5 bar (500 kPa). In a catalyst dosing vessel having a content of 100 ml, 25 ml of an alkane mixture was dosed as dilution medium. Then, 1 mmol of the scavenger tris-(pentafluorophenyl)borane $[B(C_6F_5)_3]$, dissolved in 10 ml toluene, were transferred to the reactor. After 15 minutes the desired amount of catalyst was introduced into the same catalyst dosing vessel containing again 25 ml of an alkane mixture. The resulting solution thus obtained was subsequently dosed into the reactor. The polymerization reaction was started and carried out under isothermal conditions. The ethene pressure was maintained constant at 5 bar absolute. The ethene addition was interrupted after 7 minutes and the reaction mixture was collected and quenched with methanol.

Irganox 1076™ was then added to the product as antioxidant to stabilize the polymer. The polymer was dried under vacuum at 70° C. for 24 hours. Using this general procedure 2*10$^{-5}$ moles of the polymerization catalyst 14 (see example 14) dissolved in 3 ml toluene were added to the reactor. The polymerization was carried out at a polymerization temperatures of 80° C. (results see table 1).

TABLE 1

| | catalyst | | |
|---|---|---|---|
| | 13 | 14 | 15 |
| activity [kg (PE)/g(Ti)*7 min] | 15.0 | 7.3 | 7.6 |
| M$_w$ [kg/mol] | 790 | — | — |
| MWD (M$_w$/M$_n$) | 33.1 | — | — |

Example XX

Ethylene Polymerization Using the Polymerization Catalyst 15

Using this general procedure described in example 19 1mmol of the scavenger tris-(pentafluorophenyl)borane $[B(C_6F_5)_3]$ dissolved in 10 ml toluene and 2*10$^{-5}$ moles of the polymerization catalyst 15 (see example 15) dissolved in 3 ml toluene were added to the reactor. The polymerization activity see table 1.

Example XXI

Ethylene Polymerization Using the Polymerization Catalyst 13

Using this general procedure described in example 19 1mmol of the scavenger tris-(pentafluorophenyl)borane $[B(C_6F_5)_3]$ dissolved in 10 ml toluene and 1*10$^{-5}$ moles of the polymerization catalyst 13 (see example 15) dissolved in 4 ml toluene were added to the reactor. The polymerization activity see table 1.

The obtained polymer was analysed by SEC-DV. The weight-averaged molecular weight (M$_w$) and the molecular weight distribution (MWD) was determined (see table 1).

Example XXII

Ethylene Polymerization Using the Supported Polymerization Catalyst 16

General Procedure 600 ml of an alkane mixture were brought as solvent under dry nitrogen in a stainless steel reactor having a content of 1.5 liter. The reactor was than heated under constant mixing to the required temperature of 80° C. under an absolute pressure of ethylene of 5 bar (500 kPa). In a catalyst dosing vessel having a content of 100 ml, 25 ml of an alkane mixture was dosed as dilution medium. Then, 1.5*10$^{-5}$ mol of the supported polymerization catalyst 16 (preparation see example 16) dissolved in 10 ml toluene was introduced into the same catalyst dosing vessel containing 25 ml of an alkane mixture. The resulting suspension obtained was subsequently dosed into the reactor. No additional co-catalyst or scavenger compound were added into the reactor. The polymerization reaction was thus started and carried out under isotherm conditions at 80° C. without any further use of scavanger. The ethene pressure was maintained constant at 5 bar absolute. The ethene addition was interrupted after 7 minutes and the reaction mixture was collected and quenched with methanol.

Irganox 1076™ was then added to the product as antioxidant to stabilize the polymer. The polymer was dried under vacuum at 70° C. for 24 hours. The polymerization activity see table 2. The obtained polymer was analysed by SEC-DV (weight-averaged molecular weight (M$_w$) and molecular weight distribution (MWD) see also table 2).

TABLE 2

| | polymerization[2] | | | |
|---|---|---|---|---|
| | example XXII | example XXIII | example XXIV | example XXV |
| catalyst | 16 | 17 | 18 | 16 |
| activity [kg(PE)/g(Ti)*7 min] | 6.7 (0.25)[1] | 4.0 (0.15)[1] | 4.1 (0.14)[1] | 3.0 (0.11)[1] |
| M$_w$ [kg/mol] | 1200 | 990 | 890 | — |
| MWD (M$_w$/M$_n$) | 6.9 | 7.7 | 7.2 | — |

[1] kg PE/gcat * 5 min, cat = metal complex
[2] all polymerizations were based on 0.5 g silica PQ 3030 containing 0.123 g alumium

Example XXIII

Ethylene Polymerization Using the Supported Polymerization Catalyst 17

Using this general procedure described in example 12 1.5*10$^{-5}$ mmol of supported catalyst 17 dissolved in 10 ml toluene were introduced into the reaction vessel (preparation see example 17). No additional co-catalyst or scavenger compound were added into the reactor. The polymerization activity see table 2.

The obtained polymer was analysed by SEC-DV. The weight-averaged molecular weight (M$_w$) and the molecular weight distribution (MWD) was determined (see table 2).

Example XXIV

Ethylene Polymerization Using the Supported Polymerization Catalyst 18

Using this general procedure described in example 12 1.5*10$^{-5}$ mmol of supported catalyst 18 dissolved in 10 ml toluene were introduced into the reaction vessel (preparation see example 18). No additional co-catalyst or scavenger compound were added into the reactor. The polymerization activity see table 2.

The obtained polymer was analysed by SEC-DV. The weight-averaged molecular weight ($M_w$) and the molecular weight distribution (MWD) was determined (see table 2).

Example XXV

Ethylene Polymerization Using the Polymerization Catalyst 16

600 ml of an alkane mixture were brought as solvent under dry nitrogen in a stainless steel reactor having a content of 1.5 liter. The reactor was than heated under constant mixing to the required temperature of 80° C. under an absolute pressure of ethylene of 5 bar (500 kPa).

In a catalyst dosing vessel having a content of 100 ml, 25 ml of an alkane mixture was dosed as dilution medium. Then 1 mmol of the scavenger trioctyl-aluminium dissolved in 10 ml toluene, were transferred to the reactor. After 15 minutes the $1.5*10^{-5}$ mol of the supported polymerization catalyst 16 suspended in 10 ml toluene (preparation see example 16) was introduced into the same catalyst dosing vessel containing 25 ml of an alkane mixture. The resulting suspension obtained was subsequently dosed into the reactor. No additional co-catalyst was added into the reactor. The polymerization reaction was thus started and carried out under isotherm conditions at 80° C. The ethene pressure was maintained constant at 5 bar absolute. The ethene addition was interrupted after 7 minutes and the reaction mixture was collected and quenched with methanol.

Irganox 1076™ was then added to the product as antioxidant to stabilize the polymer. The polymer was dried under vacuum at 70° C. for 24 hours. The polymerization activity see table 2.

Example XXVI

1-Hexene Polymerization Using the Polymerization Catalyst 14

600 ml of an alkane mixture were brought as solvent under dry nitrogen in a stainless steel reactor having a volume of 1.5 liter. The reactor operation was performed under an absolute pressure of ethylene of 5 bar (500 kPa).

In a catalyst dosing vessel having a content of 100 ml, 25 ml of an alkane mixture was dosed as dilution medium. Then, 1 mmol of the scavenger tris-(pentafluorophenyl) borane [$B(C_6F_5)_3$], dissolved in 10 ml toluene, were transferred to the reactor. After 15 minutes the desired amount of catalyst was introduced into the same catalyst dosing vessel containing again 25 ml of an alkane mixture. The resulting solution thus obtained was subsequently dosed into the reactor. The polymerization reaction was started and carried out under isothermal conditions. The 1-hexene pressure was maintained constant at 5 bar absolute. The 1-hexene addition was interrupted after 12 hours and the reaction mixture was collected and quenched with methanol.

Irganox 1076™ was then added to the product as antioxidant to stabilize the polymer. The polymer was dried under vacuum at 70° C. for 24 hours. Using this general procedure $2*10^{-5}$ moles of the polymerization catalyst 14 (see example 14) dissolved in 3 ml toluene were added to the reactor. The polymerizations was carried out at a polymerization temperatures of 21° C.

The obtained polymer was analysed by SEC-DV. The weight-averaged molecular weight ($M_w$) amounts to 2.9 [kg/mol] and molecular weight distribution (MWD) to 2.0.

What is claimed is:

1. Metal complex containing one or more silsesquioxane ligands, characterised in that the metal complex has the formula $$Z_y(MA_xB_q)_b \qquad (I),$$

wherein

Z is a silsesquioxane according to the formula $$R_{7-t}Si_7O_{12}YD_{1+t} \qquad (II),$$

M is a metal from groups 3–6 of the Periodic System of the Elements and the lanthanides, A is a monoanionic ligand bound to the metal, B is a π-bound ligand, y represents the number of silsesquioxane ligands and is 1–10, b represents the number of metal groups and is 1–20, q is 0,1 or 2, x is the number of substituents A bound to the metal; the value of x depends on the metal used and is equal to the valency of the metal minus 1, 2, 3 or 4, R is a substituent bound to Si, wherein the R groups can be the same or different and can for instance be hydrogen or an alkyl, aryl or silyl group, Y is an atom from group 13 or 14 of the Periodic System of the Elements, D is a group, directly bound to Y or Si with one atom from group 15 or 16 of the Periodic System of the Elements, for instance O, S, $NR^1$, $PR^1$, N= or P=, wherein $R^1$ is chosen from hydrogen, alkyl, aryl, silyl or stannyl groups, and determines the amount of substituents R and atoms D and is equal to 0, 1, 2 or 3.

2. Metal complex according to claim 1, characterised in that Z is a silsesquioxane ligand according to the formula $R_7Si_7O_{12}YD$ wherein Y, R and D have the meaning as defined in claim 1.

3. Metal complex according to claim 1, wherein Y is Si.

4. Metal complex according to claim 1, wherein the metal complex has the formula $$ZMA_xB$$

wherein Z, M, A and B have the meaning as defined in claim 1 and x is the number of substituents A bound to the metal; the value of x depends on the metal used and is equal to the valency of the metal minus 2.

5. Metal complex according to claim 1, wherein the metal complex is supported on a carrier material.

6. Metal complex according to claim 4, wherein the carrier metal is silica.

7. Process for the preparation of a metal complex according to claim 1, wherein 1 to 5 equivalents of a ligand with the formula $$R_{7-t}Si_7O_{12}Y(DR')_{1+t} \qquad (III),$$

is reacted with 1–5 equivalents $MA_xB_qX_c$ wherein the symbols have the meaning as defined in claim 1, R' is a substituent bound to D, X is a monoanionic substituent that is able to react with R' and c is 1 or 2.

* * * * *